(12) United States Patent
Suzuki et al.

(10) Patent No.: US 8,900,291 B2
(45) Date of Patent: Dec. 2, 2014

(54) MEDICAL INSTRUMENT AND METAL PRODUCT

(75) Inventors: Tetsuya Suzuki, Yokohama (JP); Kazunori Murakami, Kawasaki (JP)

(73) Assignee: Kawasumi Laboratories, Inc., Saiki-shi (JP)

( * ) Notice: Subject to any disclaimer, the term of this patent is extended or adjusted under 35 U.S.C. 154(b) by 335 days.

(21) Appl. No.: 13/390,194

(22) PCT Filed: Aug. 12, 2010

(86) PCT No.: PCT/JP2010/063703
§ 371 (c)(1),
(2), (4) Date: Mar. 22, 2012

(87) PCT Pub. No.: WO2011/021566
PCT Pub. Date: Feb. 24, 2011

(65) Prior Publication Data
US 2012/0177936 A1    Jul. 12, 2012

(30) Foreign Application Priority Data
Aug. 17, 2009 (JP) .................. 2009-188758

(51) Int. Cl.
*A61L 27/00* (2006.01)
*C23C 16/26* (2006.01)
(Continued)

(52) U.S. Cl.
CPC .............. *A61L 31/088* (2013.01); *C23C 16/26* (2013.01); *A61F 2/915* (2013.01);
(Continued)

(58) Field of Classification Search
CPC ........... A61F 2/82; A61F 2/88; A61F 2/2418; A61M 25/09; B32B 15/04; C01B 31/06; C01B 31/36

USPC ........ 428/212, 408, 457, 698; 623/1.15, 1.44, 623/1.46
See application file for complete search history.

(56) References Cited

U.S. PATENT DOCUMENTS 5,725,573 A * 3/1998 Dearnaley et al. ............ 428/698
6,572,651 B1 * 6/2003 De Scheerder et al. ...... 623/1.44
(Continued)

FOREIGN PATENT DOCUMENTS

EP        1 980 223 A1    10/2008
EP        2 018 881 A1    1/2009
(Continued)

OTHER PUBLICATIONS

Extended European Search Report issued May 24, 2013 in Patent Application No. 10809911.0.
(Continued)

*Primary Examiner* — Archene Turner
(74) *Attorney, Agent, or Firm* — Oblon, Spivak, McClelland, Maier & Neustadt, L.L.P.

(57) ABSTRACT

[Object] To provide a medical instrument capable of more effectively inhibiting a cracking and separation than conventional ones.
[Solution Means] A stent comprising a substrate layer 10 of which at least the surface is composed of a metal material, a carbon compound layer 12 that is formed so as to coat the surface of the substrate layer 10 and that contains at least one metal element, a first DLC layer 14 that is formed so as to coat the surface of the carbon compound layer 12 and that is free of fluorine, and a second DLC layer 16 that is formed so as to coat the surface of the first DLC layer 14 and that contains fluorine. The stent being constituted to satisfy the relationship defined by the expression of "A1>A2>A3", wherein A1 is a surface free energy of the carbon compound layer 12, A2 is a surface free energy of the first DLC layer 14, and A3 is a surface free energy of the second DLC layer 16.

7 Claims, 9 Drawing Sheets

(51) Int. Cl.
*A61L 31/08* (2006.01)
*A61F 2/915* (2013.01)
*A61F 2/88* (2006.01)
*A61L 31/02* (2006.01)

(52) U.S. Cl.
CPC ........... *A61F 2/88* (2013.01); *A61F 2310/0058* (2013.01); *A61L 2420/08* (2013.01); *A61L 31/022* (2013.01)
USPC .......... 623/1.15; 428/212; 428/408; 428/457; 428/698; 623/1.44; 623/1.46

(56) References Cited

U.S. PATENT DOCUMENTS

| | | | |
|---|---|---|---|
| 7,820,293 B2 * | 10/2010 | Dekempeneer | 428/408 |
| 7,931,934 B2 * | 4/2011 | Nakatani et al. | 623/1.15 |
| 8,435,287 B2 * | 5/2013 | Nakatani et al. | 623/1.44 |
| 2009/0005862 A1 | 1/2009 | Nakatani et al. | |
| 2009/0209942 A1 | 8/2009 | Nakatani et al. | |

FOREIGN PATENT DOCUMENTS

| | | | |
|---|---|---|---|
| FR | 2 837 839 A1 | | 10/2003 |
| JP | 4 501965 | | 4/1992 |
| JP | 2001 29447 | | 2/2001 |
| JP | 2001-29447 A | | 2/2001 |
| JP | 2003 310744 | | 11/2003 |
| JP | 2006 521 | | 1/2006 |
| JP | 2008 230880 | | 10/2008 |
| JP | 2009 120885 | | 6/2009 |
| JP | 2009 137888 | | 6/2009 |
| JP | 2009 153586 | | 7/2009 |
| WO | 89/11836 | * | 12/1989 |
| WO | 2007 132570 | | 11/2007 |

OTHER PUBLICATIONS

International Search Report Issued Nov. 2, 2010 in PCT/JP10/63703 Filed Aug. 12, 2010.

* cited by examiner

MEDICAL INSTRUMENT AND METAL PRODUCT

TECHNICAL FIELD

This invention relates to a medical instrument and a metal product.

BACKGROUND ART

As a conventional stent, there is known a stent in which the stent surface (substrate layer surface) is coated with a fluorine-containing diamond-like carbon layer (to be sometimes abbreviated as "F-DLC layer" hereinafter) directly or through an intermediate layer (for example, see Patent Documents 1 and 2). The intermediate layer is composed of silicon, silicon carbide (SiC) or a titanium compound (titanium oxide, titanium nitride, or the like).

The above conventional stent is a stent that is excellent in antithrombogenicity and biocompatibility since the stent surface (substrate layer surface) is coated with the F-DLC layer. Further, when the above intermediate layer is provided, the adhesion between the F-DLC layer and the substrate layer can be improved, so that it is made possible, when the stent is in expansion, to inhibit the F-DLC layer to some extent from cracking and peeling as compared with a stent in which the F-DLC layer is directly coated on the stent surface.

RELATED ART DOCUMENTS

Patent Documents

[Patent Document 1] JP 2001-29447 A
[Patent Document 2] JP 2007-307085 A

SUMMARY OF THE INVENTION

Problems to be Solved by the Invention

However, when the present inventors have produced stents having a constitution similar to that of the conventional stent and observed a stent surface with SEM (scanning electron microscope) after the stent is expanded, it is observed that the F-DLC layer undergoes a cracking and separation of layer in a portion on which a stress is mainly exerted (the flexing part of a stent strut). Since the stent is placed and kept in a body for a long period of time, it is desirable to inhibit occurring the above cracking and separation for a time period before the stent is at least coated with vascular endothelial cells.

The above demand is not limited to the stent. For example, expandable/shrinkable medical instruments other than the stent, such as an embolic coil, and flexible medical instruments such as a guide wire and a lead wire for a pacemaker are also required to satisfy the above demand.

Further, the above demand is not limited to the medical instruments, either. For example, it is also demanded to inhibit a cracking and separation from occurring on metal products such as automobile parts having surfaces coated with F-DLC layers.

This invention has been made in the light of the above demands, and it is an object of this invention to provide a medical instrument and a metal product that are capable of more effectively inhibiting a cracking and separation from occurring on them than conventional ones.

Means to Solve the Problems

[1] The medical instrument (1) of this invention includes:
a substrate layer (10) of which at least the surface is composed of a metal material,
a carbon compound layer (12) that is formed so as to coat at least part of the surface of the substrate layer (10) and that contains at least one metal element or metalloid element,
a first diamond-like carbon layer (14) that is formed so as to coat at least part of the surface of the carbon compound layer (12) and that is free of fluorine, and
a second diamond-like carbon layer (16) that is formed so as to coat at least part of the surface of the first diamond-like carbon layer (14) and that contains fluorine,
the medical instrument being constituted to satisfy the relationship defined by the expression of "A1>A2>A3",
wherein A1 is a surface free energy of the carbon compound layer (12),
A2 is a surface free energy of the first diamond-like carbon layer (14), and
A3 is a surface free energy of the second diamond-like carbon layer (16).

In the medical instrument according to this invention, the fluorine-free first diamond-like carbon layer is formed between the carbon compound layer and the second diamond-like carbon layer (F-DLC layer), the adhesion between the carbon compound layer and the second diamond-like carbon layer can be improved as compared with a case where the F-DLC layer is formed directly on the carbon compound layer surface. As a result, the occurrence of a cracking and separation of layer when the medical instrument is deformed can be more effectively inhibited than in conventional medical instruments.

In the medical instrument according to this invention, the above layers formed on the substrate layer are each constituted such that the surface free energy is decreased in a stepwise manner from the substrate layer side toward the second diamond-like carbon layer side. That is, the layers are each constituted such that the difference in surface free energy does not become much large between each adjacent layers, so that the adhesion between each adjacent layers can be increased, and as a result, the occurrence of a cracking and separation can be effectively inhibited.

Thus, the medical instrument of this invention is a medical instrument that is more capable of inhibiting the occurrence of a cracking and separation than conventional instruments.

In the present specification, "a metal element" refers to an element whose simple substance has properties as a metal. Examples of the metal element include titanium and chromium.

In the present specification, further, "metalloid" refers to an element that is around a boundary between metals and non-metals in the periodic table, and that has properties of both a metal and a non-metal. Examples of the metalloid include silicon.

[2] In the medical instrument (1) recited in the above [1], preferably, the first diamond-like carbon layer (14) contains at least one same metal element or metalloid element as the metal element or metalloid element constituting the carbon compound layer (12).

In the above constitution, the surface free energy of the first diamond-like carbon layer can be relatively easily rendered smaller than that of the carbon compound layer and larger than that of the second diamond-like carbon layer, and as a result, the medical instrument of this invention can be easily produced.

[3] In the medical instrument (1) recited in the above [2], preferably, the concentration of the metal element or metalloid element constituting the first diamond-like carbon layer (14) by atomic percentage is 1% or more but 10% or less.

The above definition will be explained in detail in Embodiments later, while it is briefly explained here. When the concentration of the metal element or metalloid element constituting the first diamond-like carbon layer by atomic percentage is less than 1%, the first diamond-like carbon layer is too hard, and as a result, a cracking and separation of layer take place easily. On the other hand, when the concentration of the metal element or metalloid element constituting the first diamond-like carbon layer by atomic percentage exceeds 10%, the surface free energy comes to be too high, which leads to a defect that it is not easy to set the surface free energy at a desirable value.

In contrast, in the medical instrument recited in the above [3], the concentration of the metal element or metalloid element constituting the first diamond-like carbon layer by atomic percentage is 1% or more but 10% or less, so that the occurrence of a cracking and separation can be inhibited as much as possible, that the surface free energy never comes to be too high in any case, and that the surface free energy can be set with relative ease at a desirable value.

From the above viewpoint, more preferably, the concentration of the metal element or metalloid element constituting the first diamond-like carbon layer by atomic percentage is 3% or more but 7.5% or less.

[4] In the medical instrument (2) recited in the above [2] or [3], preferably, the first diamond-like carbon layer (24) has a constitution in which the concentration of the metal element or metalloid element constituting the first diamond-like carbon layer (24) changes in a stepwise or continuous manner from its surface of the carbon compound layer (12) side toward its surface of the second diamond-like carbon layer (16) side.

When the above constitution is employed, the adhesion between the carbon compound layer and the first diamond-like carbon layer and the adhesion between the first diamond-like carbon layer and the second diamond-like carbon layer can be further improved.

[5] In the medical instrument (1) recited in any one of the above [2] to [4], preferably, the carbon compound layer (12) is formed of silicon carbide, and the first diamond-like carbon containing at least silicon layer (14) is formed of diamond-like carbon.

When the above constitution is employed, the medical instrument of this invention can be produced with comparative ease and inexpensively.

[6] In the medical instrument (3) recited in any one of the above [1] to [5], preferably, the second diamond-like carbon layer (36) has a constitution in which the ratio of fluorine and carbon (F/C) constituting the inside of the second diamond-like carbon layer (36) changes in a stepwise or continuous manner from its surface of the first diamond-like carbon layer (14) side toward the surface of the second diamond-like carbon layer (36).

When the above constitution is employed, antithrombogenicity and biocompatibility at sufficient levels can be obtained while maintaining the high adhesion between the first diamond-like carbon layer and the second diamond-like carbon layer.

[7] In the medical instrument (1) recited in any one of the above [1] to [6], preferably, the second diamond-like carbon layer (16) has a layer thickness of 10 nm or more but less than 300 nm.

When the layer thickness of the second diamond-like carbon layer is less than 10 nm, it is not easy to stably form the second diamond-like carbon layer by a high-frequency plasma CVD method, etc. On the other hand, when the layer thickness of the second diamond-like carbon layer is 300 nm or more, a cracking and separation of layer easily takes place when the medical instrument is deformed.

In contrast, in the medical instrument recited in the above [7], it is determined that the second diamond-like carbon layer should have a layer thickness of 10 nm or more but less than 300 nm, so that the second diamond-like carbon layer can be relatively stably formed and that the occurrence of a cracking and separation can be inhibited as much as possible.

From the above viewpoint, more preferably, it is determined that the second diamond-like carbon layer should have a layer thickness of 50 nm or more but 250 nm or less.

[8] The medical instrument (1) as recited in any one of the above [1] to [7], wherein the medical instrument is an expandable/shrinkable medical instrument including a stent and an embolic coil, or a flexible medical instrument including a guide wire and a lead wire for a pacemaker.

When the above constitution is employed, the medical instrument is excellent in the capability of more effectively inhibiting the occurrence of a cracking and separation than conventional ones, even when it is subjected to expansion/shrink or is bent.

[9] The metal product (4) of this invention includes:
a substrate layer (40) formed of a metal material,
a carbon compound layer (42) that is formed so as to coat at least part of the surface of the substrate layer (40) and that contains at least one metal element or metalloid element,
a first diamond-like carbon layer (44) that is formed so as to coat at least part of the surface of the carbon compound layer (42) and that contains fluorine,
a second diamond-like carbon layer (46) that is formed so as to coat at least part of the first diamond-like carbon layer (44) and that contains fluorine,
the metal product being constituted to satisfy the relationship defined by the expression of "A1>A2>A3",
wherein A1 is a surface free energy of the carbon compound layer (42),
A2 is a surface free energy of the first diamond-like carbon layer (44), and
A3 is a surface free energy of the second diamond-like carbon layer (46).

In the metal product according to this invention, the fluorine-free first diamond-like carbon layer is formed between the carbon compound layer and the second diamond-like carbon layer (F-DLC layer), and the above layers on the substrate layer are each constituted such that the surface free energy comes to be smaller in a stepwise manner from the substrate layer side to the second diamond-like carbon layer side, so that, for the same reasons as those described in the above [1], the adhesion between each adjacent layers can be improved, and that the occurrence of a cracking and separation can be effectively inhibited.

Thus, the metal product of this invention is a metal product that is more capable of effectively inhibiting the occurrence of a cracking and separation than conventional ones.

In the present specification, the "metal product" refers to a product that is composed mainly of a metal material but that precludes a medical instrument.

[10] In the metal product (4) recited in the above [9], preferably, the first diamond-like carbon layer (44) contains at least one same metal element or metalloid element as the metal element or metalloid element constituting the carbon compound layer (42).

When the above constitution is employed, the surface free energy of the first diamond-like carbon layer can be relatively easily rendered smaller than that of the carbon compound layer and larger than that of the second diamond-like carbon layer, and as a result, the metal product of this invention can be easily produced.

[11] In the metal product (4) recited in the above [10], preferably, the concentration of the metal element or metalloid element constituting the first diamond-like carbon layer (44) by atomic percentage is 1% or more but 10% or less.

When the concentration of the above metal element or metalloid element constituting the first diamond-like carbon layer by atomic percentage is less than 1%, the first diamond-like carbon layer is too hard, and as a result, a cracking and separation take place easily. On the other hand, when the concentration of the above metal element or metalloid element constituting the first diamond-like carbon layer by atomic percentage exceeds 10%, the surface free energy comes to be too high, which leads to a defect that it is not easy to set the surface free energy at a desirable value.

In contrast, in the metal product recited in the above [11], the concentration of the metal element or metalloid element constituting the first diamond-like carbon layer by atomic percentage is 1% or more but 10% or less, so that the occurrence of a cracking and separation can be inhibited as much as possible, that the surface free energy comes to be never too high in any case, and that the surface free energy can be set with relative ease at a desirable value.

From the above viewpoint, more preferably, the concentration of the metal element or metalloid element constituting the first diamond-like carbon layer by atomic percentage is 3% or more but 7.5% or less.

[12] In the metal product (4) recited in any one of the above [9] to [11], preferably, the carbon compound layer (42) is composed of silicon carbide, and the first diamond-like carbon layer (44) is composed of a diamond-like carbon containing at least silicon.

When the above constitution is employed, the metal product of this invention can be produced with relative ease and inexpensively.

The features of the medical instruments (medical instrument of this invention) recited in the above [4], [6] and [7] can be applied to the metal products (metal product of this invention) recited in the above [9] to [12].

Parenthesized reference numerals added to terms or wordings in claims or this section (Means to Solve the Problems) are used for making it easier, with reference to drawings, to understand what are described in claims or this section, and shall not impose any limitation on technical contents described in claims or this section.

Advantageous Effect of the Invention

In the medical instrument or metal product according to this invention, the fluorine-free first diamond-like carbon layer is formed between the carbon compound layer and the second diamond-like carbon layer (F-DLC layer), so that the adhesion between the carbon compound layer and the second diamond-like carbon layer can be improved as compared with a case where the F-DLC layer is formed directly on the carbon compound layer and that the occurrence of a cracking and separation of layer can be more effectively inhibited when the medical instrument or the metal product is deformed than in conventional ones.

In the medical instrument or metal product according to this invention, the layers (carbon compound layer, first diamond-like carbon layer and second diamond-like carbon layer) formed on the substrate layer have a constitution in which the surface free energy comes to be smaller in a stepwise manner from the substrate layer side toward the second diamond-like carbon layer side, so that the adhesion between each adjacent layers can be improved, and that the occurrence of a cracking and separation of layer can be inhibited.

EMBODIMENTS FOR CARRYING OUT THE INVENTION

The medical instrument and metal product of this invention will be explained on the basis of Embodiments shown in Figures.

Embodiment 1

First Embodiment of the Invention

Embodiment 1 will explain the medical instrument of this invention with reference to a stent as one example of the expandable/shrinkable medical instrument. The constitution of the stent 1 in Embodiment 1 will be explained with reference to FIGS. 1 and 2.

Figure 1:
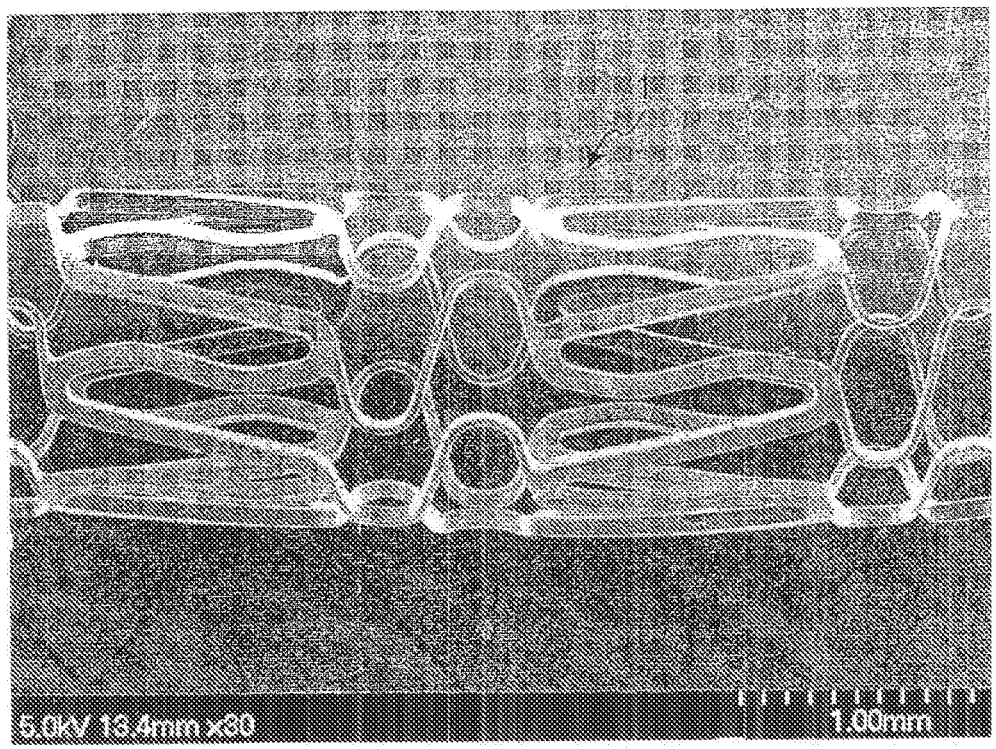
FIG. 1 is a photograph as a substitute for drawings for showing the appearance of the stent 1 in Embodiment 1.
Figure 2:
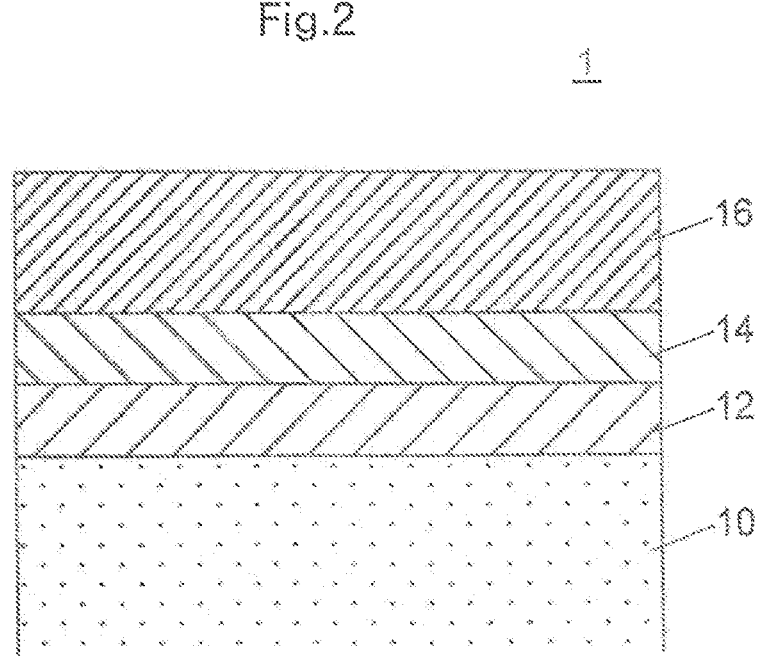
FIG. 2 is a schematic drawing for showing the constitution (layer constitution) of the stent 1 in Embodiment 1.

FIG. 1 is a photograph as a substitute for drawings for showing the appearance of the stent 1 in Embodiment 1. FIG. 2 is a schematic drawing for showing the constitution (layer constitution) of the stent 1 in Embodiment 1.

As shown in FIG. 2, the stent in Embodiment 1 has a substrate layer 10, a carbon compound layer 12 formed on the surface of the substrate layer 10, a first diamond-like carbon layer ("first DLC layer" hereinafter) 14 formed so as to coat the surface of the carbon compound layer 12 and a second diamond-like carbon layer ("second DLC layer" hereinafter) 16 formed so as to coat the surface of the first DLC layer 14. The stent 1 is, for example, a balloon expandable stent.

The substrate layer 10 is a layer at least the surface of which is formed of a metal material. The metal material can be selected, for example, from stainless steel, cobalt chromium alloy, titanium, titanium alloy, tantalum, tantalum alloy, platinum, platinum alloy, gold, gold alloy, etc. As a stainless steel, for example, SUS316L excellent in corrosion resistance is preferred. The substrate layer 10 in Embodiment 1 is composed of SUS316L.

The carbon compound layer 12 is a layer formed of a carbon compound containing at least one metal element or metalloid element. The carbon compound can be selected, for example, from silicon carbide (SiC), titanium carbide (TiC), chromium carbide ($Cr_3C_2$) and titanium silicon carbide ($Ti_3SiC_2$). The carbon compound layer 12 in Embodiment 1 is a silicon carbide layer.

It is determined that the carbon compound layer 12 should have a thickness of 50 nm to 150 nm (e.g., 100 nm).

The first DLC layer 14 is a layer composed of a diamond-like carbon, and it is a layer that does not contain fluorine but contains the same metal element or metalloid element as at least one element of the metal element or metalloid element constituting the carbon compound layer 12. That is, when the carbon compound layer is a titanium carbide layer, the first DLC layer is a diamond-like carbon layer containing a predetermined amount of titanium (e.g., Ti-DLC, etc.). When it is a titanium silicon carbide layer, the first DLC layer is a diamond-like carbon layer containing a predetermined amount of at least silicon (e.g., Si-DLC, etc.), or a diamond-like carbon layer containing a predetermined amount of at least titanium (e.g., Ti-DLC, etc.). The first DLC layer 14 in Embodiment 1 is a diamond-like carbon layer containing a predetermined amount of silicon (Si-DLC).

It is determined that the concentration of silicon constituting the first DLC layer 14, by atomic percentage, should be 1% or more but 10% or less (e.g., 4-5%).

It is determined that the first DLC layer 14 should have a thickness of 50 nm to 150 nm (e.g., 100 nm).

The second DLC layer 16 is a diamond-like carbon layer that is a fluorine-containing layer (F-DLC). It is determined that the ratio of fluorine and carbon (F/C) constituting an inside of the second DLC layer 16 should be 10% or more but 60% or less.

It is determined that the second DLC layer 16 should have a thickness of 10 nm or more but less than 300 nm (e.g., 200 nm).

In the stent 1 according to Embodiment 1, the stent 1 is constituted to satisfy the expression of "A1>A2>A3" in which the surface free energy of the carbon compound layer 12 is A1, the surface free energy of the first DLC layer 14 is A2 and the surface free energy of the second DLC layer 16 is A3.

In the stent 1 according to Embodiment 1, having the above described constitution, the fluorine-free first DLC layer 14 is formed between the carbon compound layer 12 and the second DLC layer 16, so that the adhesion between the carbon compound layer 12 and the second DLC layer 16 can be improved as compared with a case where the F-DLC layer is formed directly on the carbon compound layer. As a result, when the stent 1 is expanded, the occurrence of a cracking and separation of layer can be more effectively inhibited than in conventional ones.

In the stent 1 according to Embodiment 1, the above layers formed on the substrate layer 10 are each constituted such that the surface free energy decreases in a stepwise manner from the substrate layer 10 side toward the second DLC layer 16 side. That is, they have a constitution in which the difference between the surface free energies of any adjacent layers is kept not to become much larger as possible, so that the adhesion between any adjacent layers can be increased, and as a result, the occurrence of a cracking and separation of layer can be effectively inhibited.

The stent 1 according to Embodiment 1 is a stent that is capable of more effectively inhibiting the occurrence of a cracking and separation than conventional ones.

In the stent 1 according to Embodiment 1, the first DLC layer 14 contains the same metal element or metalloid element as the metal element or metalloid element (silicon in Embodiment 1) constituting the carbon compound layer 12. In this manner, it is relatively easier to render the surface free energy of the first DLC layer 14 smaller than that of the carbon compound layer 12 and larger than that of the second DLC layer 16, and as a result, the stent 1 according to Embodiment 1 can be easily produced or put into practice.

In the stent 1 according to Embodiment 1, it is determined that the concentration of silicon constituting the first DLC layer 14, by atomic percentage, should be 1% or more but 10% or less, so that the occurrence of a cracking and separation of layer (delamination) can be inhibited to the highest decreases. And it is also made possible that the surface free energy never come to be too high in any case, and that the surface free energy can be set at a desirable value with relative ease.

In the stent 1 according to Embodiment 1, the carbon compound layer 12 is formed of silicon carbide, and the first DLC layer 14 is formed of silicon-containing diamond-like carbon (Si-DLC), so that the stent 1 according to Embodiment 1 can be produced with relative ease and inexpensively.

Meanwhile, when the ratio of fluorine and carbon (F/C) constituting the inside of the second DLC layer is less than 10%, the second DLC layer becomes too hard, and as a result, a cracking and separation of layer are liable to occur. On the other hand, when the F/C ratio inside the second DLC layer comes to be larger than 60%, the layer comes to be a layer with low crystallinity and with relative fragility, which leads to a easy cracking and separation of the layer.

In the stent 1 according to Embodiment 1, it is determined that the ratio of fluorine and carbon (F/C) constituting the inside of the second DLC layer 16 should be 10% or more but 60% or less, so that the occurrence of a cracking and separation of layer can be inhibited and minimized as much as possible.

In the stent 1 according to Embodiment 1, it is determined that the second DLC layer 16 should have a thickness of 10 nm or more but less than 300 nm, so that the formation of second DLC layer 16 can be made relatively stably, and that the occurrence of a cracking and separation of layer can be inhibited to a highest degree.

(Method for Producing Stent 1 According to Embodiment 1)

The method for producing the stent 1 (method for producing a stent according to Embodiment 1) will be explained with reference to FIG. 3.

Figure 3:
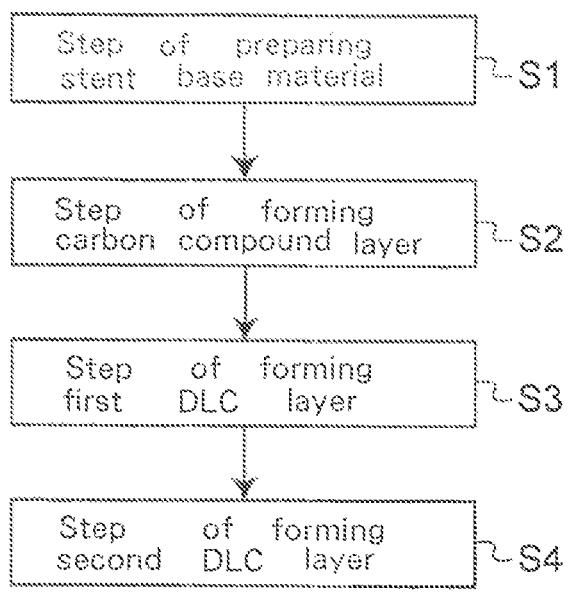
FIG. 3 is a flow chart for explaining a method of producing the stent 1.

FIG. 3 is a flow chart for explaining the method for producing the stent 1.

As shown in FIG. 3, the method for producing the stent 1 includes the step S1 of preparing a stent base material, the step S2 of forming a carbon compound layer, the step S3 of forming a first DLC layer and the step S4 of forming a second DLC layer in this order. These steps will be explained one by one hereinafter.

1. Step S1 of Preparing Stent Base Material.

A stent base material having the above stent substrate layer 10 is prepared first. The stent substrate can be selected from known metal materials. The form of the above stent base material is not specially limited. For example, it may be a structure having a constitution of a cylinder (tube) formed by folding a small-gage metal wire in a zigzag form or consisting of network system.

2. Step S2 of Forming Carbon Compound Layer

Then, a carbon compound layer 12 is formed on the surface of the prepared stent base material (substrate layer 10). The method for forming the carbon compound layer 12 can be selected from known methods such as chemical vapor deposition methods (CVD) typified by a thermal CVD method and a plasma CVD method (including a high-frequency plasma CVD method), and physical vapor deposition methods typified by a sputtering method and an ion-plating method. When the high-frequency plasma CVD method is selected from the above-described examples for forming the carbon compound layer 12 formed of silicon carbide (SiC), there may be employed a constitution in which the stent base material is set in a high-frequency plasma CVD apparatus and subjected to argon bombardment treatment under predetermined conditions, and then using, for example, tetramethylsilane (TMS) as feed gas, the carbon compound layer 12 is formed until it comes to have a predetermined thickness. A substance other than tetramethylsilane may be used as a silicon source.

3. Step S3 of Forming First DLC Layer

Then, a first DLC layer 14 is formed on the surface of the carbon compound layer 12. The method for forming the first DLC layer 14 can be selected from known methods such as chemical vapor deposition methods typified by a plasma CVD method (including a high-frequency plasma CVD method) and physical vapor deposition methods (PVD) typified by various sputtering methods, an ion-plating method, an ion beam vapor deposition method and a plasma ion implantation method. When the high-frequency plasma CVD method is selected from the above-described examples for forming the first DLC layer 14 formed of diamond-like carbon containing a predetermined amount of silicon (Si-DLC), there may be employed a constitution or procedure in which the stent base material with the carbon compound layer 12 formed on it is set in a high-frequency plasma CVD apparatus, the first DLC layer 14 is formed using, for example, tetramethylsilane (TMS) and acetylene ($C_2H_2$) as feed gases until it comes to have a predetermined thickness. A substance other than tetramethylsilane may be used as a silicon source. A substance (e.g., benzene ($C_6H_6$)) other than acetylene may be used as a carbon source.

4. Step S4 for Forming Second DLC Layer

Then, a second DLC layer 16 is formed on the surface of the first DLC layer 14. The method for forming the second DLC layer 16 can be selected from those methods which are described as examples with regard to the step S3 for forming the first DLC layer. When the high-frequency plasma CVD method is selected for forming the second DLC layer 16 formed of diamond-like carbon containing a predetermined amount of fluorine (F-DLC), there may be employed a constitution or procedure in which the stent base material having the carbon compound layer 12 and the first DLC layer 14 formed is set in a high-frequency plasma CVD apparatus, the second DLC layer 16 is formed using, for example, perfluoropropane ($C_3F_8$) and acetylene ($C_2H_2$) as feed gasses until it comes to have a predetermined thickness.

Substances (e.g., tetrafluoromethane ($CF_4$) and hexafluoroethane ($C_2F_6$) other than perfluoropropane may be used as a fluorine source. Further, substances (e.g., benzene ($C_6H_6$)) other than acetylene may be used as carbon sources.

By carrying out the above steps, the stent 1 according to Embodiment 1 can be produced.

Embodiment 2

Second Embodiment of the Invention

Figure 4:
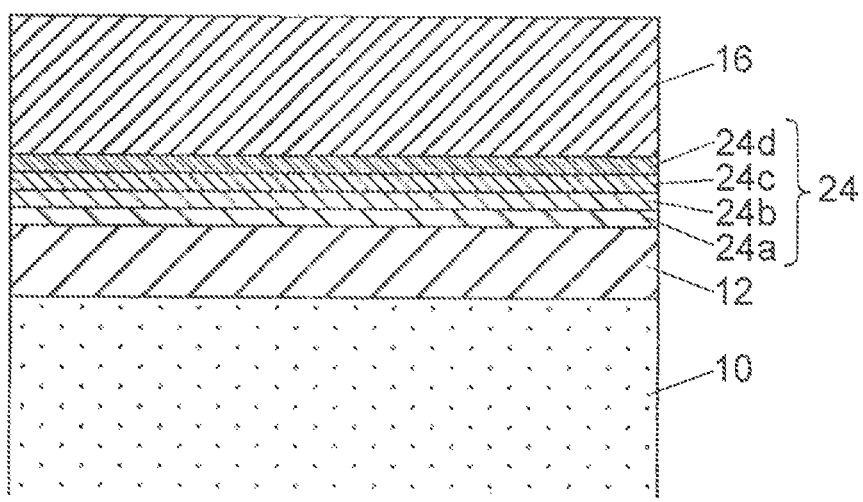
FIG. 4 is a schematic drawing for showing the constitution (layer constitution) of the stent 2 in Embodiment 2.

FIG. 4 schematically shows the constitution (layer constitution) of a stent 2 according to Embodiment 2. In FIG. 4, the same reference numerals are used for identifying the same members in FIG. 2, and detailed explanations thereof will be omitted.

The stent 2 according to Embodiment 2 has a constitution very similar to that of the stent 1 according to Embodiment 1, while the constitution of a first DLC layer 24 differs from that of the stent 1 according to Embodiment 1 and has a multi-layered constitution.

In the stent 2 according to Embodiment 2, the first DLC layer 24 is constituted of four layers such as a first layer 24a to a fourth layer 24d as shown in FIG. 4. The first DLC layer 24 is formed of Si-DLC like the first DLC layer 14 explained in Embodiment 1, and it has a constitution that satisfies $B1 \geq B2 \geq B3 \geq B4$ (provided that a case of $B1=B2=B3=B4$ is excluded) in which B1 to B4 are concentrations of silicon constituting the first layer 24a to the fourth layer 24d by atomic percentage. In other words, the first DLC layer 24 is constituted such that the concentration of silicon constituting the first DLC layer 24, by atomic percentage, changes in a stepwise manner from its surface of the carbon compound layer 12 side toward its surface of the second DLC layer 16 side.

The stent 2 according to Embodiment 2 has a constitution in which the surface free energy of the first layer 24a of the first DLC layer 24 is smaller than the surface free energy of the carbon compound layer 12 and the surface free energy of the fourth layer 24d of the first DLC layer 24 is larger than the surface free energy of the second DLC layer 16.

While the stent 2 according to Embodiment 2 differs from the stent 1 according to Embodiment 1 in constitution of the fluorine-free first DLC layer 24 is formed as explained above, the first DLC layer 24 free of fluorine is formed between the carbon compound layer 12 and the second DLC layer 16, and the above layers formed on the substrate layer 10 have a constitution in which the surface free energy comes to be smaller in a stepwise manner from the substrate layer 10 side toward the second DLC layer 16 side, like the stent 1 according to Embodiment 1, thereby the resulting stent is capable of more effectively inhibiting the occurrence of a cracking and separation than conventional ones.

In the stent 2 according to Embodiment 2, the first DLC layer 24 has a constitution in which the concentration of silicon constituting the first DLC layer 24, by atomic percentage, changes in a stepwise manner from its surface of the carbon compound layer 12 side to its surface of the second DLC layer 16 side as described above. In this manner, the adhesion between the carbon compound layer 12 and the first DLC layer 24 and the adhesion between the first DLC layer 24 and the second DLC layer 16 can be further improved.

Having a constitution similar to that of the stent 1 according to Embodiment 1 except that the first DLC layer has a different layer constitution, the stent 2 according to Embodiment 2 has the same concerned or corresponding effects as those which are produced by the stent 1 according to Embodiment 1.

The method for producing the stent 2 (process for producing a stent according to Embodiment 2) in principle includes the step S1 of preparing a stent base material to the step S4 of forming the second DLC layer like the method for producing the stent 1 (process for producing a stent according to Embodiment 1), while it differs from the method for producing the stent 1 in the content of the step S3 of forming the first DLC layer.

That is, in the method for producing the stent 2, there may be employed a constitution in which the stent base material with the carbon compound layer 12 formed thereon is placed in the high-frequency plasma CVD apparatus when the high-frequency plasma CVD method is selected in the step S3 of forming the first DLC layer and while it is set therein, the above first layer 24a to the fourth layer 24d (first DLC layer 24) are formed using, for example, tetramethylsilane (TMS) and acetylene ($C_2H_2$) as feed gases and by changing, in a stepwise manner, the flow ratio (partial pressure ratio) of tetramethylsilane and acetylene in a predetermined manner (timing), under predetermined conditions.

Embodiment 3

Third Embodiment of the Invention

Figure 5:
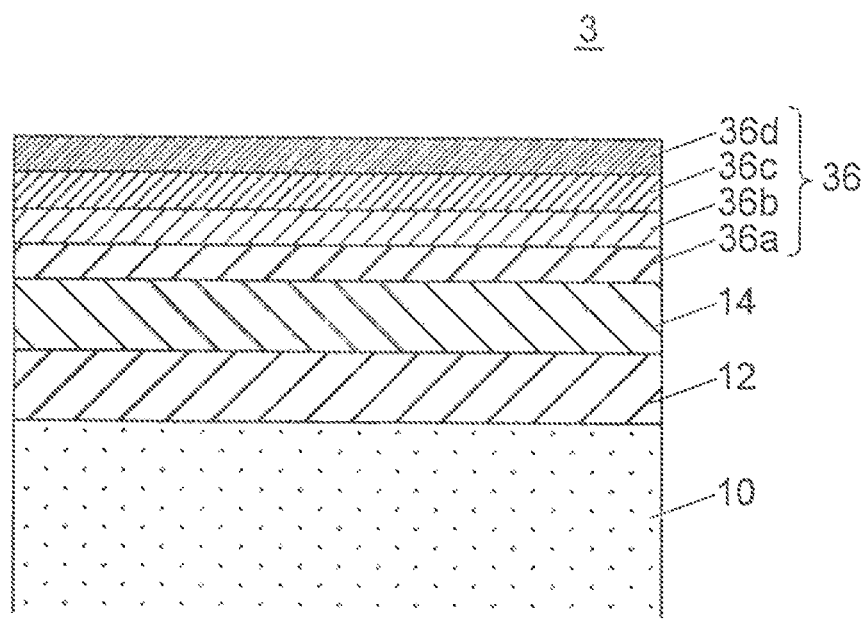
FIG. 5 is a schematic drawing for showing the constitution (layer constitution) of the stent 3 in Embodiment 3.

FIG. 5 schematically shows the constitution (layer constitution) of a stent 3 according to Embodiment 3. In FIG. 5, the same reference numerals are used for identifying the same members in FIG. 2, and detailed explanations thereof will be omitted.

The stent 3 according to Embodiment 3 has a constitution very similar to that of the stent 1 according to Embodiment 1, while the constitution of a second DLC layer 36 differs from that of the stent 1 according to Embodiment 1, in that having a multi-layered constitution.

In the stent 3 according to Embodiment 3, the second DLC layer 36 is constituted of four layers such as a first layer 36a to a fourth layer 36d as shown in FIG. 5. The second DLC layer 36 is formed of F-DLC like the second DLC layer 16 as explained in Embodiment 1, and it has a constitution that satisfies C1≤C2≤C3≤C4 (provided that a case of C1=C2=C3=C4 is excluded) in which C1 to C4 are ratios of fluorine and carbon (F/C) constituting the inside of the first layer 36a to the fourth layer 36d. In other words, the second DLC layer 36 has a constitution in which the ratio of fluorine and carbon (F/C) within the second DLC layer 36 changes in a stepwise manner from its surface of the first DLC layer 14 side toward the surface of the second DLC layer 36.

The stent 3 according to Embodiment 3 has a constitution in which the surface free energy of the first layer 36a of the second DLC layer 36 is smaller than the surface free energy of the first DLC layer 14.

The stent 3 according to Embodiment 3 differs from the stent 1 according to Embodiment 1 in the constitution of the second DLC layer as described above, while the fluorine-free first DLC layer 14 is formed between the carbon compound layer 12 and the second DLC layer 36 like the stent 1 according to Embodiment 1, and each of the above layers formed on the substrate layer 10 has a constitution in which the surface free energy comes to be smaller from the substrate layer 10 side toward the second DLC layer 36 side, so that it is provided a stent that is capable of more effectively inhibiting the occurrence of a cracking and separation than conventional ones.

In the stent 3 according to Embodiment 3, the second DLC layer 36 has a constitution in which the ratio of fluorine and carbon (F/C) constituting the inside of the second DLC layer 36 changes in a stepwise manner from its surface of the first DLC layer 14 side toward its surface of the second DLC layer 36. In this manner, the adhesion between the first DLC layer 14 and the second DLC layer 36 can be improved, and at the same time, there provided antithrombogenicity and biocompatibility at sufficient levels.

The method for producing the stent 3 (method for producing the stent according to Embodiment 3) in principle includes the same step of preparing a stent base material (S1) to the step of forming the second DLC layer (S4) like the method for producing the stent 1 (process for producing the stent according to Embodiment 1), while, the content of the step of forming the second DLC layer (S4) differs from the method for producing the stent 1.

That is, in the method for producing the stent 3, there may be employed a constitution in which the stent base material with the carbon compound layer 12 and the first DLC layer 14 formed thereon is placed in the high-frequency plasma CVD apparatus when the high-frequency plasma CVD method is selected in the step S4 of forming the second DLC layer and while it is set therein, the above first layer 36a to the fourth layer 36d (second DLC layer 36) are formed using, for example, perfluoropropane ($C_3F_8$) and acetylene ($C_2H_2$) as feed gases and by changing, in a stepwise manner, the flow ratio (partial pressure ratio) of perfluoropropane and acetylene in a predetermined manner (timing), under predetermined conditions.

Embodiment 4

Fourth Embodiment of the Invention

In Embodiment 4, a coil spring that is an automobile part for a suspension will be explained as an example of the metal product of this invention.

Figure 6A:
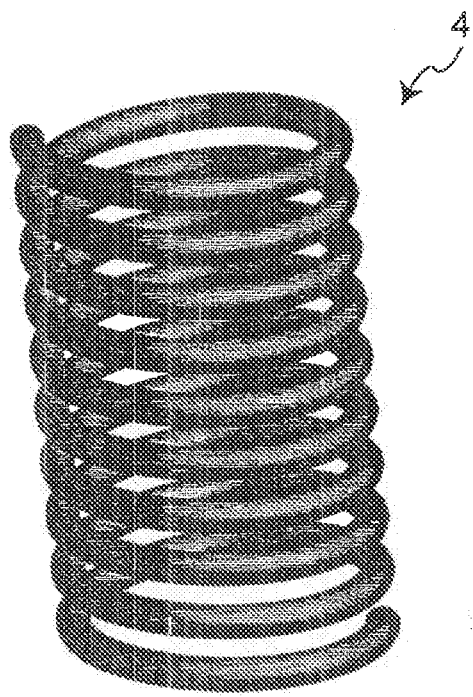
FIG. 6 shows a drawing and drawing for explaining a coil spring 4 in Embodiment 4.
Figure 6B:
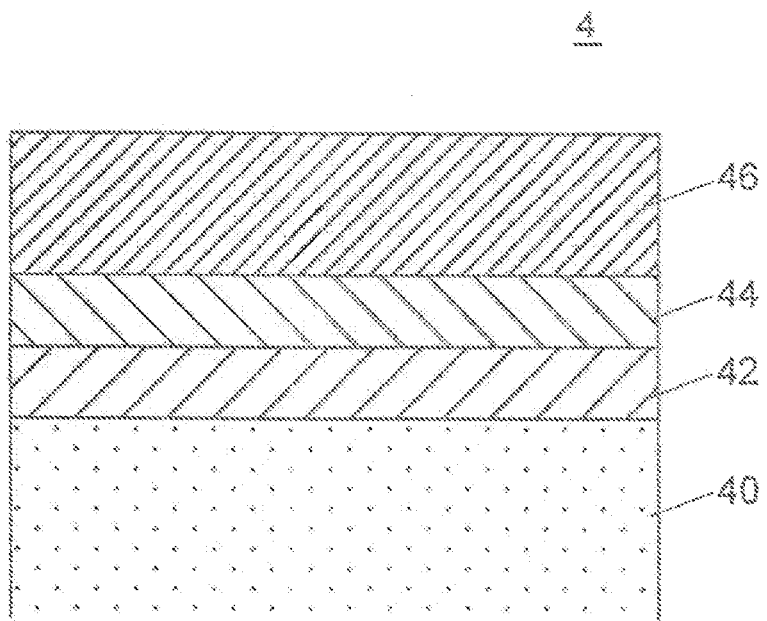

FIG. 6 shows a drawing for explaining a coil spring 4 according to Embodiment 4. FIG. 6A shows an appearance of the coil spring 4, and FIG. 6B schematically shows the constitution (layer constitution) of the coil spring 4.

As shown in FIG. 6, the coil spring 4 according to Embodiment 4 has a substrate layer 40, a carbon compound layer 42 formed of the surface of the substrate layer 40, a first DLC layer 44 formed so as to coat the surface of the carbon compound layer 42 and a second DLC layer 46 formed so as to coat the first DLC layer 44.

The substrate layer 40 is a layer formed of a metal material. The metal material includes, for example, stainless steel or spring steel. The substrate layer 40 in Embodiment 4 is composed of stainless steel (e.g., SUS316L).

The carbon compound layer 42 is a layer composed of a carbon compound containing at least one metal element or metalloid element. The carbon compound can be selected, for example, from silicon carbide (SiC), titanium carbide (TiC), chromium carbide ($Cr_3C_2$) and titanium silicon carbide ($Ti_3SiC_2$) et al. The carbon compound layer 42 in Embodiment 4 is a silicon carbide layer.

It is determined that the carbon compound layer 42 should have a thickness of 50 nm to 150 nm (e.g., 100 nm).

The first DLC layer 44 is a layer composed of diamond-like carbon, and it is a layer that contains no fluorine but contains at least one same metal element or metalloid element as the metal element or metalloid element constituting the carbon compound layer 42. The first DLC layer 44 in Embodiment 4 is a diamond-like carbon layer containing a predetermined amount of silicon (Si-DLC).

It is determined that the concentration of silicon constituting the first DLC layer 44, by atomic percentage, should be 1% or more but 10% or less (e.g., 4-5%).

It is determined that the first DLC layer 44 should have a layer thickness of 50 nm to 150 nm (e.g., 100 nm).

The second DLC layer 46 is a layer that is composed of diamond-like carbon and that contains fluorine (F-DLC). It is determined that the ratio of fluorine and carbon (F/C) constituting the inside of the second DLC layer 46 should be 10% or more but 60% or less.

It is determined that the second DLC layer 46 should have a layer thickness of 10 nm or more but less than 300 nm (e.g., 200 nm).

In the coil spring 4 according to Embodiment 4, the coil spring 4 is so constituted as to satisfy "A1>A2>A3" in which the surface free energy of the carbon compound layer 42 is A1, the surface free energy of the first DLC layer 44 is A2 and the surface free energy of the second DLC layer 46 is A3.

In the above-constituted coil spring 4 according to Embodiment 4, the fluorine-free first DLC layer 44 is formed between the carbon compound layer 42 and the second DLC layer 46, so that the adhesion between the carbon compound layer 42 and the second DLC layer 46 can be improved as compared with a case where the F-DLC layer is formed directly on the carbon compound layer. As a result, the occurrence of a cracking and separation of layer when the coil spring 4 is deformed can be more effectively inhibited than conventional ones.

In the coil spring 4 according to Embodiment 4, each of the above layers formed on the substrate layer 40 has a constitution in which the surface free energy decreases in a stepwise manner from the substrate layer 40 side toward the second DLC layer 46 side. That is, the above layers are constituted such that the difference in surface free energy does not become much large between each adjacent layers, so that the adhesion between each adjacent layers can be kept at a higher value, and as a result, the occurrence of a cracking and separation of layer can be inhibited.

Thus, the coil spring 4 according to Embodiment 4 is a coil spring that is capable of more effectively inhibiting the occurrence of a cracking and separation than conventional ones.

In the coil spring 4 according to Embodiment 4, the first DLC layer 44 contains the same metal element or metalloid element (silicon in Embodiment 4) as the metal element or metalloid element constituting the carbon compound layer 42. In this manner, the surface free energy of the first DLC layer 44 can be rendered smaller than that of the carbon compound layer 42 and larger than the second DLC layer 46, and as a result, the coil spring 4 according to Embodiment 4 can be easily produced.

In the coil spring 4 according to Embodiment 4, it is determined that the concentration of silicon constituting the first DLC layer 44, by atomic percentage, should be 1% or more but 10% or less, so that the occurrence of a cracking and separation of layer (delamination) can be inhibited as much as possible, that the surface free energy never comes to be too high in any case, and that the surface free energy can be set at a desirable value with relative ease.

In the coil spring 4 according to Embodiment 4, the carbon compound layer 42 is composed of silicon carbide, and the first DLC layer 44 is composed of a silicon-containing diamond-like carbon (Si-DLC), so that the coil spring 4 according to Embodiment 4 can be produced with relative ease and inexpensively.

In the coil spring 4 according to Embodiment 4, it is determined that the ratio of fluorine and carbon (F/C) constituting the inside of the second DLC layer 46 is 10% or more but 60% or less, so that the occurrence of a cracking and separation of layer can be inhibited as much as possible.

In the coil spring 4 according to Embodiment 4, it is determined that the second DLC layer 46 should have a thickness of 10 nm or more but less than 300 nm, so that the second DLC layer 46 can be relatively stably formed and that the occurrence of a cracking and separation of layer can be inhibited as much as possible.

The coil spring 4 according to Embodiment 4 can be produced by carrying out the coil spring preparation step of preparing a coil spring base material, the carbon compound layer formation step of forming the carbon compound layer 42 on the surface of the coil spring base material (substrate layer 40), the first DLC layer formation step of forming the first DLC layer 44 on the surface of the carbon compound layer 42 and the second DLC layer formation step of forming the second DLC layer 46 on the surface of the first DLC layer 44 in this order like the same process of producing the stent 1 explained in Embodiment 1 although its detailed explanation will be omitted.

The medical instrument and metal product of this invention have been explained hereinabove on the basis of Embodiments thereof, while this invention shall not be limited to these Embodiments, and can be practiced in various embodiments so long as they do not deviate from the gist of this invention, and for example, the following variants can be employed.

(1) The above Embodiment 2 has explained the case where the first DLC layer is composed of four layers, while this invention shall not be limited thereto, and there may be employed a constitution in which the first DLC layer is composed of two, three, five, or more layers, and the concentration of metal element of metalloid element (e.g., silicon) constituting the first DLC layer, by atomic percentage, is changed in a stepwise manner from its surface of the second DLC layer side toward the carbon compound layer. Further, the above Embodiment 2 has explained the case where the first DLC layer with regard to an example of the first DLC layer 24 in which the concentration of silicon by atomic percentage is changed in a stepwise manner, while this invention shall not be limited thereto. The first DLC layer may have a constitution in which the concentration of silicon constituting the first DLC layer, by atomic percentage, is continuously changed from its surface of the second DLC layer toward the surface of the carbon compound layer.

(2) The above Embodiment 2 has explained the case having a constitution in which the surface free energy of the first layer 24a is smaller than that of the carbon compound layer 12 and a constitution in which the surface free energy of the fourth layer 24d is greater than that of the second DLC layer 16, while this invention shall not be limited thereto. For example, there may be employed a constitution in which the surface free energy of the first layer 24a is nearly equal to that of the carbon compound layer 12 and the surface free energy of the fourth layer 24d is nearly equal to that of the second DLC layer 16. In this case, the second and third layers 24b and 24c may have any constitution so long as they satisfy "(the surface free energy of the first layer 24a)>(surface free energy of the fourth layer 24d)".

(3) The above Embodiment 3 has explained the case where the second DLC layer is composed of four layers, while this invention shall not be limited thereto. There may be employed a constitution in which the second DLC layer is composed of two, three, five or more layers and the ratio of fluorine and carbon (F/C) constituting the inside of the second DLC layer is changed in a stepwise manner from its surface of the first DLC layer side toward its surface of the second DLC layer. Further, the above Embodiment 3 has explained the case wherein second DLC layer with regard to an example of the second DLC layer 36 in which the ratio of fluorine and carbon (F/C) inside each layer is changed in a stepwise manner, while this invention shall not be limited thereto. The second DLC layer may have a constitution in which the ratio of fluorine and carbon (F/C) constituting each layer of the second DLC layer is continuously changed from its surface of the first DLC layer side toward its surface of the second DLC layer.

(4) The above Embodiments 1 to 3 have explained medical instruments with regard to a balloon expandable stent as an example, while this invention shall not be limited thereto.

This invention can be applied to a self-expandable stent. Further, this invention can be also applied to a drug-eluting stent (DES).

Further, this invention can be also applied to expandable/shrinkable medical instruments other than a stent and flexible medical instruments required to have flexibility in living body. As expandable/shrinkable medical instruments other than a stent, it can be applied, for example, to an embolic coil. As flexible medical instruments, it can be applied to a guide wire and a lead wire of a pacemaker. It can be also suitably used in a portion that comes in contact with the blood vessel of an artificial heart.

(5) The above Embodiment 4 has explained the case where both the first DLC layer 44 and the second DLC layer 46 are single layers, while this invention shall not be limited thereto. The first DLC layer may have a constitution in which it is divided into a plurality of layers like the first DLC layer 24 explained in Embodiment 2 and the concentration of the metal element or metalloid element (e.g., silicon) constituting the first DLC layer, by atomic percentage, is changed in a stepwise manner from its surface of the second DLC layer side toward its surface of the carbon compound layer side. Alternatively, it may have a constitution in which the concentration of the metal element or metalloid element (e.g., silicon) constituting the first DLC layer, by atomic percentage, is continuously changed from its surface of the second DLC layer side toward its surface of the carbon compound layer side. Similarly, the second DLC layer may have a constitution in which it is divided into a plurality of layers like the second DLC layer 36 explained in Embodiment 3, and the ratio of fluorine and carbon (F/C) constituting the divided layers of the second DLC layer is changed in a stepwise manner from its surface of the first DLC layer side toward its surface of the second DLC layer. Alternatively, it may have a constitution in which the ratio of fluorine and carbon (F/C) constituting the divided layers of the second DLC layer is continuously changed from its surface of the first DLC layer side toward its surface of the second DLC layer.

(6) The above Embodiment 4 has explained the coil spring of an automobile part as an example of the metal product, while this invention shall not be limited thereto. This invention can be applied to automobile parts (e.g., shaft member, etc.) other than the coil spring and metal products other than the automobile parts such as a Thompson blade. In addition, this invention has an advantageous effect in particular when it is applied to deformable metal products such as a coil spring.

The above Embodiments have explained a medical instrument or a metal product with regard to the case where the metal element or metalloid element contained in the carbon compound layer is silicon, while this invention shall not be limited thereto. The carbon compound layer may contain a metalloid element other than silicon, or a metal element such as titanium or chromium. The metal element or metalloid element contained in the carbon compound layer is not limited to one metal element or metalloid element, and the carbon compound layer may contain a plurality of elements selected from metal elements and metalloid elements. Similarly, further, the first DLC layer has been explained with regard to an example of a diamond-like carbon containing silicon that is a metalloid element (Si-DLC), while this invention shall not be limited thereto. It may be a diamond-like carbon containing a metalloid element other than silicon or a diamond-like carbon containing a metal element such as titanium or chromium. Further, the metal element or metalloid element contained in the first DLC layer is not limited to one metal element or metalloid element, and the first DLC layer may contain a plurality of elements selected from metal elements and metalloid elements.

EXAMPLES

This invention will be more specifically explained hereinafter with regard to Examples (and Comparative Examples), while this invention shall not be limited by these Examples so long as the gist of the invention is maintained.

Example 1 and Comparative Example 1

First, the influence of the relationship of the surface free energy of the carbon compound layer, that of the first DLC layer and that of the second DLC layer on the surface state of an extended stent will be explained.

A stent that had the constitution of the stent 1 according to Embodiment 1 and that satisfied the relationship of the expression of "A1>A2>A3" was used as Example 1, and a stent that did not satisfy the relationship of the expression of "A1>A2>A3" was used Comparative Example 1. (In the expression, A1: surface free energy of carbon compound layer, A2: surface free energy of first DLC layer, A3: surface free energy of second DLC layer)

For calculating the surface free energy of each layer in Example 1, there were prepared a sample (Sample P-1) in which only a carbon compound layer was formed on the surface of a stent base material, a sample (Sample P-2) in which two layers of a carbon compound layer and a first DLC layer were formed on the surface of a stent base material and a sample (Sample P-3) in which three layers of a carbon compound layer, a first DLC layer and a second DLC layer were formed on the surface of a stent base material, and the surface free energy values of the samples were taken as surface free energies of each of the layers constituting Example 1.

For calculating the surface free energy of each layer in Comparative Example 1, there were prepared a sample (Sample Q-1) in which only a carbon compound layer was formed on the surface of a stent base material, a sample (Sample Q-2) in which two layers of a carbon compound layer and a DLC layer composed only of diamond-like carbon were formed on the surface of a stent base material, and a sample (Sample Q-3) in which a carbon compound layer, a DLC layer composed only of diamond-like carbon and a second DLC layer were formed on the surface of a stent base material, and the surface free energy values of the samples were taken as surface free energies of each of the layers constituting Comparative Example 1.

(1) Layer Constitution of Each Sample (a) Example

Sample P-1 is a sample (SiC) obtained by forming a silicon carbide layer (SiC layer) as a carbon compound layer on the surface of a stent base material (substrate layer).

Sample P-2 is a sample (SiC/Si-DLC) obtained by forming an SiC layer on a stent base material (substrate layer) and forming a silicon-containing DLC layer (Si-DLC layer) as a first DLC layer on the surface thereof.

Sample P-3 is a sample (SiC/Si-DLC/F-DLC) obtained by forming an SiC layer on a stent base material (substrate layer), forming an Si-DLC layer on the surface of the SiC layer and forming a fluorine-containing DLC layer (F-DLC layer) as a second DLC layer on the surface thereof.

(b) Comparative Example

Sample Q-1 is a sample (SiC) similar to the sample P-1.

Sample Q-2 is a sample (SiC/DLC) obtained by forming a silicon carbide layer (SiC layer) on the surface of a stent base material (substrate layer) and forming a DLC layer composed of only Si-free (free of silicon) diamond-like carbon on the surface thereof.

Sample Q-3 is a sample (SiC/DLC/F-DLC) obtained by forming an SiC layer on the surface of a stent base material (substrate layer), forming an Si-free DLC layer on the surface of the SiC layer and forming a fluorine-containing DLC layer (F-DLC layer) as a second DLC layer on the surface thereof.

(2) Methods for Producing Those Samples (Sample P-1)

In the production of Sample P-1, first, a stent base material composed of SUS316L was prepared, and the stent base material was set in a high-frequency plasma CVD apparatus (Model "YH-1200", Onwardgiken Co., LTD., Japan). Then, argon bombardment treatment was carried out under predetermined reduced pressure conditions for 10 minutes, and then an SiC layer was formed on the surface of the stent base material (substrate layer) using tetramethylsilane (TMS) as a feed gas. In this case, the gas flow rate and the reaction time period were adjusted as required such that the SiC layer should have a thickness of 100 nm.

(Sample P-2)

In the production of Sample P-2, after the steps for Sample P-1 were carried out in the same manner, an Si-DLC layer was formed on the surface of the SiC layer using tetramethylsilane (TMS) and acetylene ($C_2H_2$) as feed gases. In this case, the gas flow rates and the reaction time period were adjusted as required such that the Si-DLC layer should have a thickness of 100 nm. The ratio of flow rate of tetramethylsilane to the total sum of the flow rate of tetramethylsilane and the flow rate of acetylene ("TMS partial pressure" hereinafter) was adjusted to 4%.

(Sample P-3)

In the production of Sample P-3, after the steps for Sample P-2 were carried out in the same manner, an F-DLC layer was formed on the surface of the Si-DLC layer using perfluoropropane ($C_3F_8$) and acetylene ($C_2H_2$) as feed gases. In this case, the gas flow rates and the reaction time period were adjusted as required such that the F-DLC layer should have a thickness of 200 nm.

(Samples Q-1-Q-3)

In the production of Sample Q-1, the steps for Sample P-1 were carried out in the same manner.

In the production of Sample Q-2, after the steps for Sample Q-1 (P-1) were carried out in the same manner, a DLC layer was formed on the surface of the SiC layer using acetylene ($C_2H_2$) as a feed gas. In this case, the gas flow rate and the reaction time period were adjusted as required such that the DLC layer should have a thickness of 100 nm.

In the production of Sample Q-3, after the steps for Sample Q-2 were carried out in the same manner, an F-DLC layer was formed on the surface of the DLC layer using perfluoropropane ($C_3F_8$) and acetylene ($C_2H_2$) as feed gases. In this case, the gas flow rates and the reaction time period were adjusted as required such that the F-DLC layer should have a thickness of 200 nm.

(3) Method of Calculating Surface Free Energy

The calculation of a surface free energy refers to a method of calculating a solid surface free energy according to the Owens-Wendt method. In this method, liquids having different surface tensions are used, contact angles of each liquid are measured, and a dispersion component, a polar component and a hydrogen bond component are calculated on the basis of the Young-Dupre's equation. Further, a surface free energy (surface tension) is derived from the dispersion component, polar component and hydrogen bond component on the basis of the extended Fowkes equation. As the above liquids having different surface tensions, water and diiodomethane ($CH_2I_2$) were used.

(4) Evaluation of Expanded Stent for Surface State

Sample P-3 was used as a stent of Example 1, and Sample Q-3 was used as a stent of Comparative Example 1. The stents of Example 1 and Comparative Example 1 were expanded with a balloon catheter until they were diameter ϕ3.5 mm large (ϕ1.5 mm before the expansion). The expanded stents were observed through SEM, and each of the expanded stents was evaluated of a surface state on the basis of whether or not they had a cracking and separation of layer.

(Observations of Results)

Figure 7A:
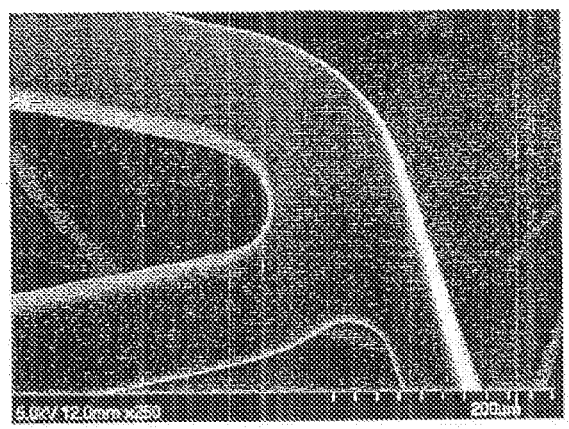
FIG. 7 shows SEM photographs of a stent surface in Example 1 as a substitute for drawings.
Figure 7B:
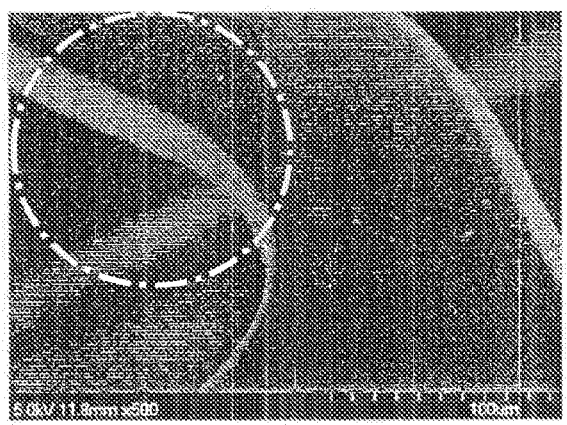
Figure 7C:
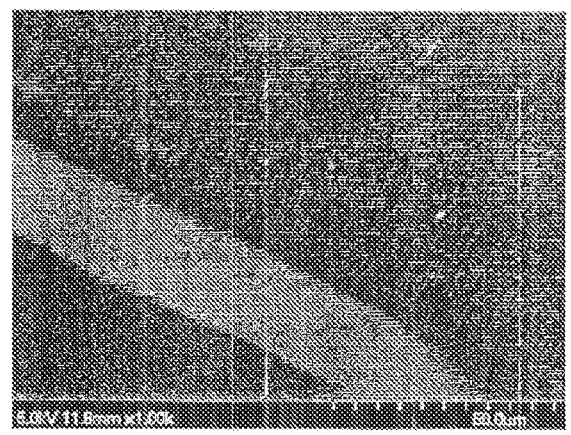
Figure 8A:
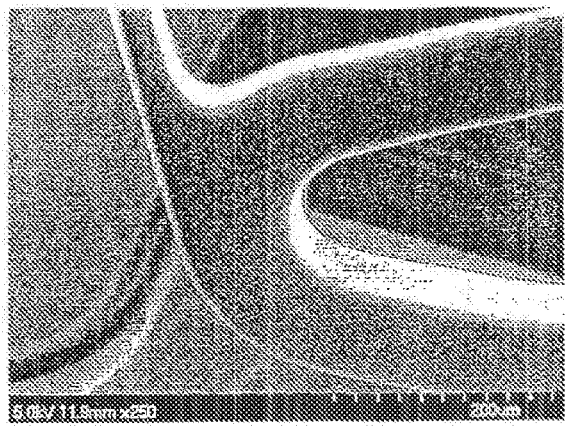
FIG. 8 shows SEM photographs of a stent surface in Comparative Example 1 as a substitute for drawings.
Figure 8B:
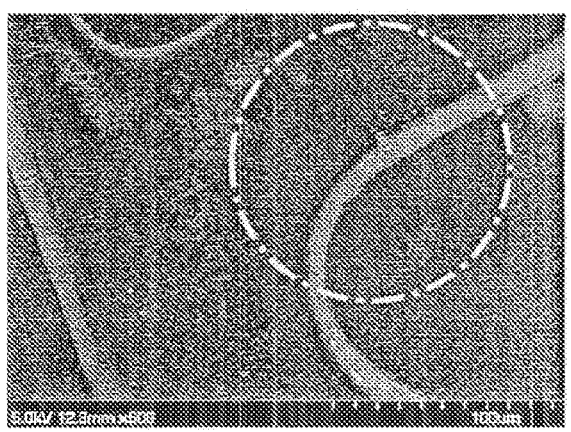
Figure 8C:
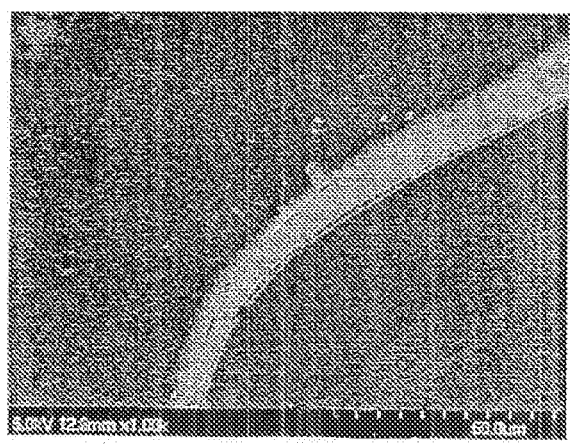

Table 1 shows the results of calculation of surface free energies of layers of Example 1 and Comparative Example 1. Further, FIG. 7 shows SEM photographs of surface of the stent of Example 1, and FIG. 8 shows SEM photographs of surface of the stent of Comparative Example 1. FIG. 7A and FIG. 8A are SEM photographs (magnification for observation: ×250) taken of surface states of the stents before their expansion, and FIG. 7B and FIG. 8B are SEM photographs (magnification for observation: ×500) taken of surface states of the stents after their expansion. FIG. 7C and FIG. 8C are SEM photographs (magnification for observation: ×1,000) taken by enlarging those portions which were surrounded by an alternate long and short dash line in FIG. 7B and FIG. 8B. In addition, FIGS. 7 and 8 are photographs taken of surfaces of flexed portions of stent strut parts.

TABLE 1

| | Sample No. | Contact angle average value (degree) (N = 5) | | Surface free energy [mJ/m$^2$] |
|---|---|---|---|---|
| | | H$_2$O | CH$_2$I$_2$ | |
| Example 1 | P-1(SiC) | 61.0 | 42.0 | 47.0 (=A1) |
| | P-2(Si-DCL) | 74.6 | 41.0 | 41.7 (=A2) |
| | P-3(F-DLC) | 84.7 | 65.9 | 28.2 (=A3) |
| Comparative Example 1 | Q-1(SiC) | 61.0 | 42.0 | 47.0 (=A1) |
| | Q-2(DLC) | 62.1 | 35.9 | 48.3 (=A2) |
| | Q3(F-DLC) | 84.7 | 65.9 | 28.2 (=A3) |

With regard to the surface free energy of each layer, as is seen in Table 1, the stent of Example 1 has a constitution that satisfies the relationship defined by the expression of "A1>A2>A3", while the stent of Comparative Example 1 does not have any constitution that satisfies the relationship of "A1>A2>A3", but its constitution is "A2>A1>A3".

When the surface states of the expanded stents are compared, it was found that the stent of Example 1 was free from the occurrence of a cracking and separation of layer as is clearly shown in FIGS. 7B and 7C. In contrast, it was found that the stent of Comparative Example 1 suffered the occurrence of a cracking and separation of layer as is clearly shown in FIGS. 8B and 8C.

It has been confirmed that when the surface state of an expanded stent and the surface free energy of each layer are correlated so as to satisfy the relationship of expression of "A1>A2>A3", the occurrence of a cracking and separation of layer can be more effectively inhibited than conventional ones.

Example 2

Example 2 will explain various physical properties when the concentration of a metal element or metalloid element constituting the first DLC layer, by atomic percentage, is changed.

As samples, there were used nine kinds of test pieces obtained by forming SiC layers (carbon compound layers) and Si-DLC layers (first DLC layers) on the surfaces of ultra-hard tungsten carbide (WC) plates having the form of a square each as a planar view (size: 12.5 mm×12.5 mm×4.0 mm thickness).

The above nine kinds of test pieces refer to samples (Samples R-1 to R-9) that were produced each by setting the TMS partial pressure at nine stages of 0%, 1.0%, 2.0%, 3.0%, 4.0%, 5.0%, 7.5%, 10.0% and 20.0% when Si-DLC layers were formed, with each test piece having different Si concentrations. The steps for producing these Samples are the same as those explained in Example 1, and hence a detailed explanation thereof is omitted.

The concentration of silicon constituting the Si-DLC layer in each Sample by atomic percentage ("Si concentration" hereinafter) was measured by an X-ray electron spectroscopy (XPS). For evaluating Samples for physical properties, each Sample was measured for a hardness, a Young's modulus and a surface free energy (evaluation items).

Figure 9:
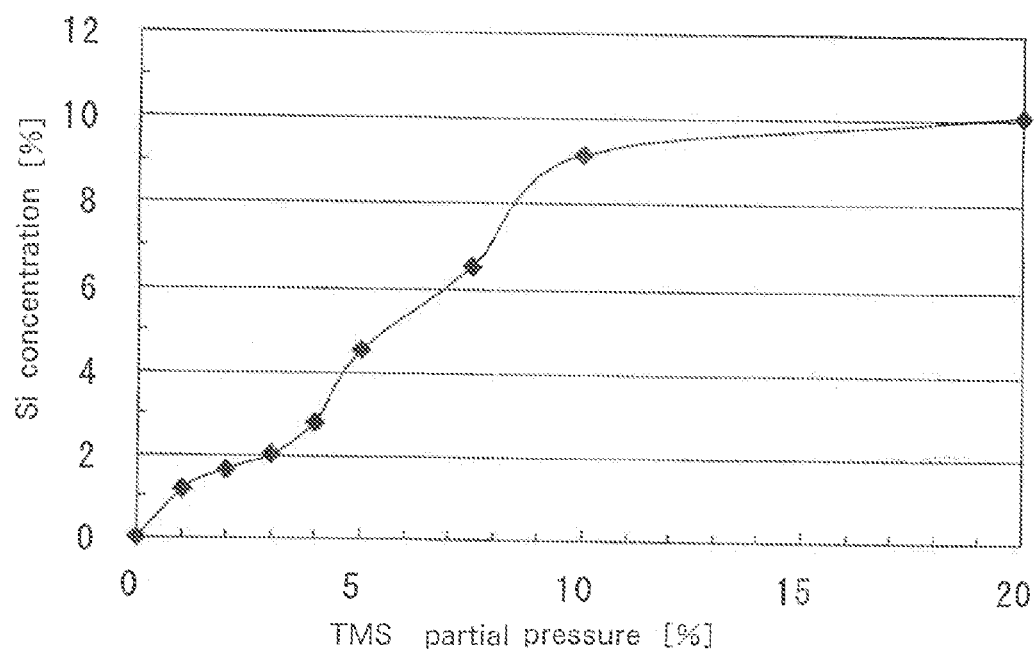
FIG. 9 shows a drawing giving relationship between TMS partial pressure and Si concentration.
Figure 10:
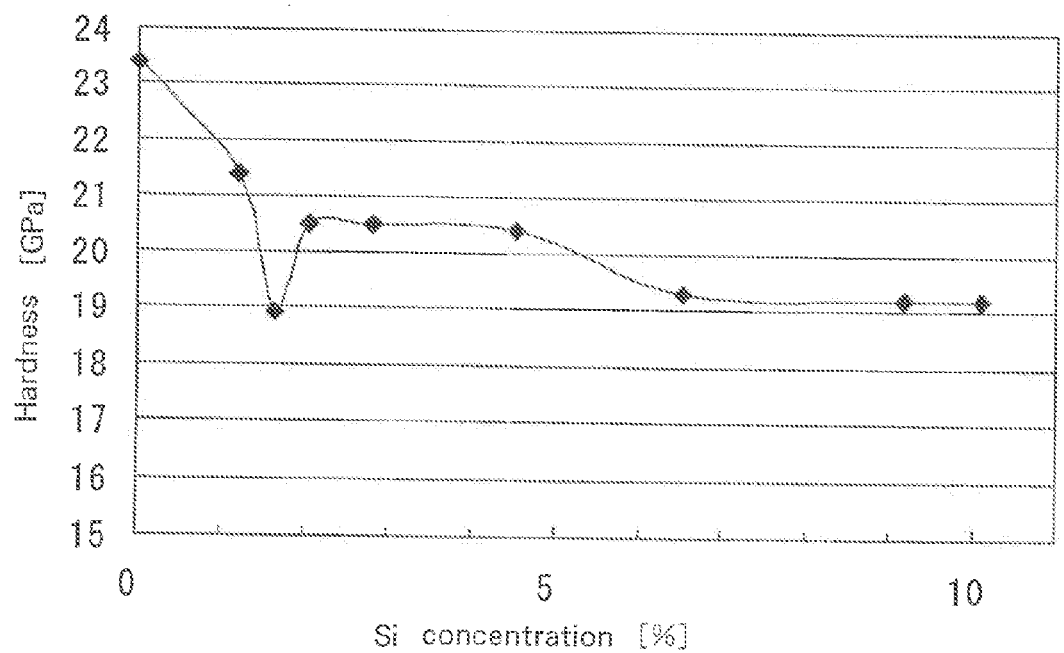
FIG. 10 shows a drawing giving relationship between Si concentration and hardness.
Figure 11:
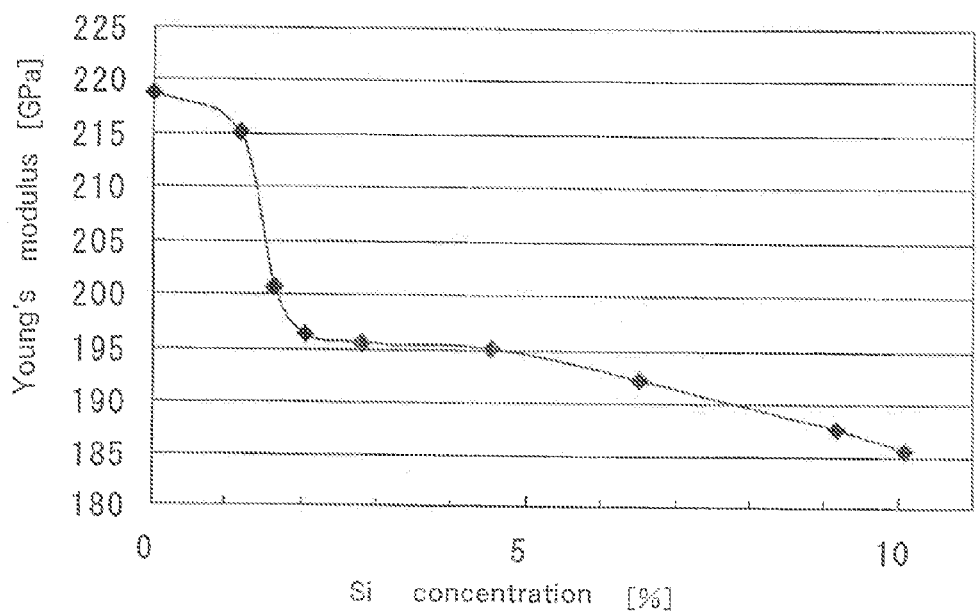
FIG. 11 shows a drawing giving relationship between Si concentration and young's modulus.
Figure 12:
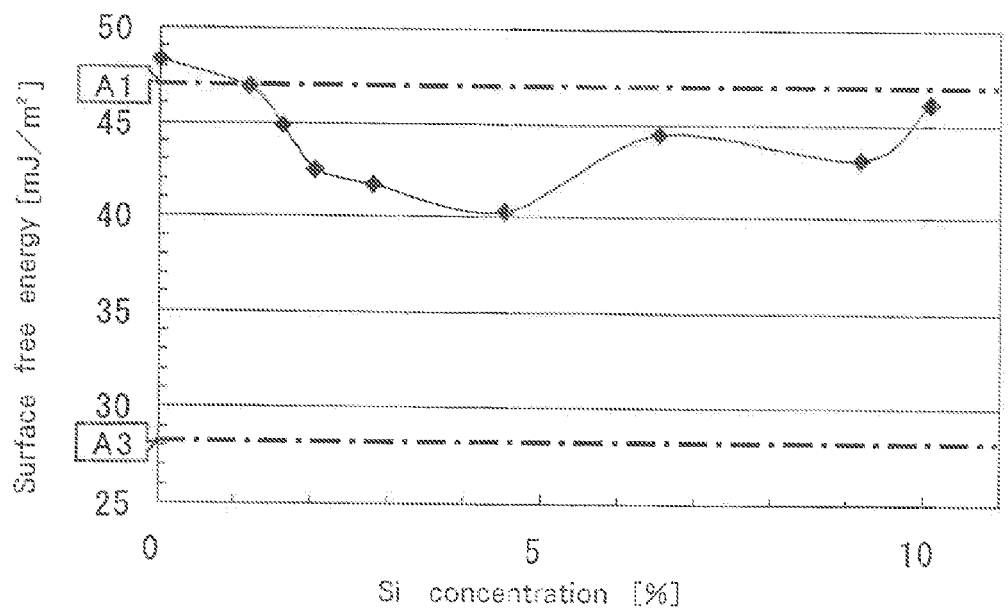
FIG. 12 shows a drawing giving relationship between Si concentration and surface free energy.
Figure 13A:
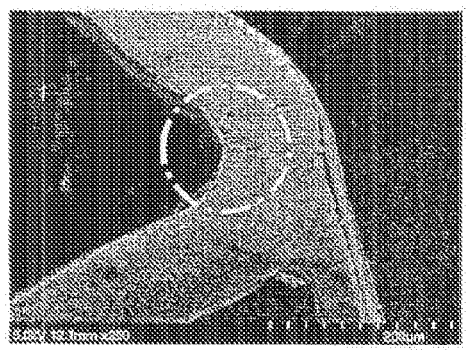
FIG. 13 shows SEM photographs of a stent surface in Example 3 as a substitute for drawings.
Figure 13B:
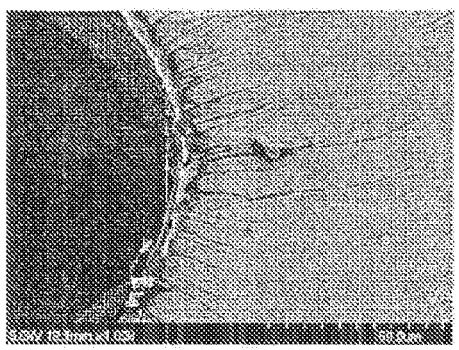
Figure 13C:
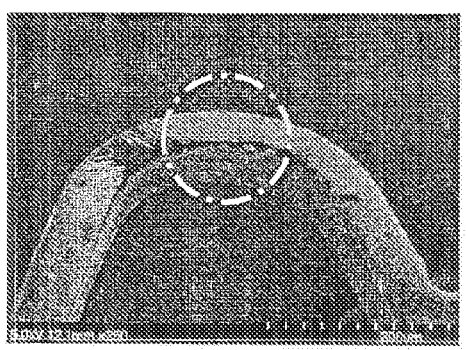
Figure 13D:
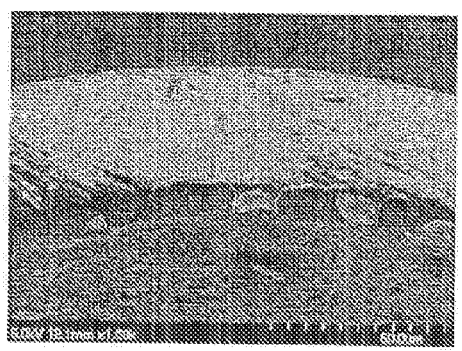

Table 2 shows the results of measurements of each Sample for a hardness, a Young's modulus and a surface free energy. Further, FIG. 9 shows the relationship between the TMS partial pressure and the Si concentration, FIG. 10 shows the relationship between the Si concentration and the hardness, FIG. 11 shows the relationship between the Si concentration and the Young's modulus, and FIG. 12 shows the relationship between the Si concentration and the surface free energy.

TABLE 2

| Sample No. | TMS partial pressure [%] | Si concentration [%] | Hardness [GPa] | Young's modulus [GPa] | Surface free energy [mJ/m$^2$] |
|---|---|---|---|---|---|
| R-1 | 0 | 0 | 23.4 | 218.8 | 48.3 |
| R-2 | 1.0 | 1.20 | 21.4 | 215.1 | 46.9 |
| R-3 | 2.0 | 1.64 | 18.9 | 200.7 | 44.9 |
| R-4 | 3.0 | 2.05 | 20.5 | 196.3 | 42.5 |
| R-5 | 4.0 | 2.80 | 20.5 | 195.6 | 41.7 |
| R-6 | 5.0 | 4.53 | 19.8 | 191.5 | 40.3 |
| R-7 | 7.5 | 6.52 | 19.3 | 192.3 | 44.4 |
| R-8 | 10.0 | 9.18 | 19.2 | 187.6 | 43.1 |
| R-9 | 20.0 | 10.1 | 19.2 | 185.6 | 46.1 |

(Observations of Results)
(TMS Partial Pressure and Si Concentration)

With regard to the relationship between the TMS partial pressure and the Si concentration, it has been recognized that as shown in Table 2 and in FIG. 9, the Si concentration shows values nearly equal to those of the TMS partial pressure in the range of TMS partial pressure of 0 to 10%, and that the Si concentration does not increase easily when the TMS partial pressure goes over 10%.

(Si Concentration and Hardness)

With regard to the relationship between the Si concentration and the hardness, it has been recognized as shown in Table 2 and in FIG. 10 that the hardness is 23.4 GPa when the Si concentration is 0%, but that the hardness is about 20 GPa when the Si concentration is in the range of approximately 1 to 10%, and that the value of the hardness decreases with the increase in the Si concentration. However, when the Si concentration comes to be over about 7%, no change has been recognized in the hardness of the Si-DLC layer.

(Si Concentration and Young's Modulus)

With regard to the relationship between the Si concentration and the Young's modulus, it has been recognized as shown in Table 2 and in FIG. 11 that the Young's modulus tends to decrease with the increase in the Si concentration.

(Si Concentration and Surface Free Energy)

With regard to the relationship between the Si concentration and the surface free energy, it has been recognized as shown in Table 2 and in FIG. 12 that the surface free energy tends to decrease when the Si concentration is in the range of 5% or less, and that the surface free energy gradually increases where the Si concentration exceeds 5%. Further, when the Si concentration is approximately 4-5%, the surface free energy showed a pattern of reaching a minimum value.

As shown in the above Table 1, the surface free energy (A1) of the SiC layer as a carbon compound layer is 47.0 mJ/m$^2$, and the surface free energy (A3) of the F-DLC layer as a second DLC layer was 28.2 mJ/m$^2$, so that those samples which satisfy the relationship defined by the expression of "A1>A2>A3" are Sample R-2 to Sample R-9 as shown in Table 2 and in FIG. 12. That is, it has been found that the relationship of the expression of "A1>A2>A3" is satisfied so long as the Si concentration is approximately 1 to 10%.

It has been also found that when the Si concentration is approximately 2 to 6%, relatively low values of the surface free energy are given.

Further, when the Si concentration is in the range of 5% or more, the surface free energy shows a pattern of increasing with the increase in the Si concentration, so that it is assumed that the surface free energy comes to be too high when the Si concentration exceeds 10%.

CONCLUSION

From the above results, the following (A) to (D) have been confirmed.

(A) Even if the TMS partial pressure is made larger than 10% in the above production method, the Si concentration of the first DLC layer is not so increased.

(B) When the Si concentration is adjusted to 1% or more, a relatively soft layer is formed. However, even if the Si concentration is made larger than 7%, there is produced basically no difference in the softness of the layer.

(C) When the Si concentration is adjusted to 1% or more, a relatively extendable layer (layer that can easily follow the extension of other layer) is formed.

(D) When the Si concentration is approximately 1 to 10%, the relationship defined by the expression of "A1>A2>A3" is satisfied. When the Si concentration is adjusted to approximately 2 to 6%, the surface free energy is relatively low as a value. When the Si concentration exceeds 10%, it is no longer easy to satisfy the relationship defined by the expression of "A1>A2>A3".

It has been confirmed from these that when the Si concentration is 1% or more but 10% or less, not only the occurrence of a cracking and separation of layer can be inhibited as much as possible, but also the surface free energy never comes to be too high in any case, and that the surface free energy can be set at a desirable value with relative ease.

Example 3

Example 3 will explain the influence that the thickness of the second DLC layer exerts on the surface state of the expanded stent.

A stent sample obtained by forming an SiC layer (carbon compound layer), an Si-DLC layer (first DLC layer) and an F-DLC layer (second DLC layer) on the surface of a stent base material was used as a sample, and the thickness of the F-DLC layer was set at 300 nm for the sample. As compared with the stent (Sample P-3) of the above Example 1 of which the F-DLC layer had a thickness of 200 nm, it is seen that the F-DLC layer of the stent of Example 3 was arranged to have a larger thickness. The steps for producing the sample were the same as those explained in Example 1, and a detailed explanation thereof will be omitted.

Since it is not easy to form any F-DLC layer having a thickness of less than 10 nm by a high-frequency plasma CVD method, no sample of which the F-DLC layer has a thickness of less than 10 nm has been produced.

The above stent was expanded with a balloon catheter until it had a diameter of $\phi 3.5$ mm ($\phi 1.5$ mm before expansion). Then, the expanded stent was observed through SEM, and it was observed for a surface state depending upon whether or not the surface had a cracking and separation of layer.

FIG. 13 shows SEM photographs of the surface of the stent of Example 3. FIGS. 13A and 13C are SEM photographs (magnification for observation: X250) taken of surface state of the stent after its expansion, FIG. 13B is an SEM photograph (magnification for observation: X500) taken by enlarging a portion surrounded by an alternate long and short dash line in FIG. 13A, and FIG. 13D is an SEM photograph (magnification for observation: X1,000) taken by enlarging a portion surrounded by an alternate long and short dash line in FIG. 13C. In addition, FIG. 13 shows photographs taken of surfaces of flexed portions of the stent strut part.

In the stent of which the F-DLC layer was arranged to have a thickness of 300 nm, the occurrence of a cracking (e.g., see FIG. 13B) and separation of layer (e.g., see FIG. 13D) was recognized as is clear in FIG. 13.

Meanwhile, the stent (Sample P-3) of the above Example 1 was a stent of which the F-DLC layer was arranged to have a thickness of 200 nm, and the occurrence of a cracking and separation of layer was not recognized as will be easily understood by reference to FIGS. 7B and 7C.

It has been confirmed from the above that when it is determined that the second DLC layer should have a thickness of 10 nm or more but less than 300 nm, the second DLC layer can be relatively stably formed, and that the occurrence of a cracking and separation of layer can be inhibited as much as possible.

INDUSTRIAL UTILITY

In the medical instrument according to this invention, the occurrence of a cracking and separation of layer can be more inhibited than conventional ones. Therefore, when this invention is applied, for example, to a stent, the occurrence of a cracking and separation of layer can be inhibited at least for a time period before the stent is covered with blood vessel endothelial cells, and the medical instrument of this invention thus has remarkably high utility when used in the medical field. Further, the metal product of this invention is similarly capable of more inhibiting the occurrence of a cracking and separation of layer than conventional ones, so that it can be utilized not only in automobile parts such as a coil spring, but also in very broad technical fields of metal parts such as a Thompson blade other than automobile parts.

EXPLANATIONS OF REFERENCE NUMERALS 1-3 Stent
4 Coil spring
10, 40 Substrate layer
12, 42 Carbon compound layer
14, 24, 44 first DLC layer
16, 36, 46 second DLC layer
24a-24d first to fourth layers (of first DLC layer)
36a-36d first to fourth layers (of second DLC layer)

The invention claimed is:

1. A medical instrument, comprising:
a substrate layer of which at least a surface comprises a metal material;
(i) a carbon compound layer comprising silicon carbide, wherein the carbon compound layer is formed so as to coat at least part of the surface of the substrate layer;
(ii) a first diamond-like carbon layer comprising silicon, wherein the first diamond-like carbon layer is free of fluorine and is formed so as to coat at least part of a surface of the carbon compound layer; and
(iii) a second diamond-like carbon layer comprising fluorine, wherein the second diamond-like carbon layer is formed so as to coat at least part of a surface of the first diamond-like carbon layer,
wherein the concentration of silicon in the (ii) first diamond-like carbon layer is 1% or more and 10% or less by atomic percentage,
among the (i) carbon compound layer, the (ii) first diamond-like carbon layer, and the (iii) second diamond-like carbon layer, the medical instrument satisfies a relationship defined by the expression: A1>A2>A3, such that:
A1 is a surface free energy of the carbon compound layer;
A2 is a surface free energy of the first diamond-like carbon layer; and
A3 is a surface free energy of the second diamond-like carbon layer, and
an occurrence of cracking and separation of the (i) carbon compound layer, the (ii) first diamond-like carbon layer, and the (iii) second diamond-like carbon layer is effectively prevented in the medical instrument.

2. The medical instrument of claim 1, wherein, in the (ii) first diamond-like carbon layer, the concentration of silicon changes in a stepwise or continuous manner from the surface of the (i) carbon compound layer side toward its surface on the (iii) second diamond-like carbon layer side.

3. The medical instrument of claim 1, wherein, in the (iii) second diamond-like carbon layer, a ratio of fluorine and carbon (F/C) constituting an inside of the (iii) second diamond-like carbon layer changes in a stepwise or continuous manner from its surface on the (ii) first diamond-like carbon layer side toward its surface on the (iii) second diamond-like carbon layer side.

4. The medical instrument claim 1, wherein the (iii) second diamond-like carbon layer has a layer thickness of 10 nm or more and less than 300 nm.

5. The medical instrument of claim 1, wherein the medical instrument is:
an expandable/shrinkable medical instrument further comprising a stent and an embolic coil; or a flexible medical instrument further comprising a guide wire and a lead wire for a pacemaker.

6. The medical instrument of claim 1, wherein the (iii) second diamond-like carbon layer is free of silicon.

7. A metal product, comprising:
a substrate layer comprising a metal material;
(i) a carbon compound layer comprising silicon carbide, wherein the carbon compound layer is formed so as to coat at least part of a surface of the substrate layer;
(ii) a first diamond-like carbon layer comprising silicon, wherein the first diamond-like carbon layer is free of fluorine and is formed so as to coat at least part of a surface of said carbon compound layer; and
(iii) a second diamond-like carbon layer comprising fluorine, wherein the second diamond-like carbon layer is formed so as to coat at least part of said first diamond-like carbon layer,
wherein the concentration of silicon in the (ii) first diamond-like carbon layer is 1% or more and 10% or less by atomic percentage,
among the (i) carbon compound layer, the (ii) first diamond-like carbon layer, and the (iii) second diamond-like carbon layer, the metal product satisfies a relationship defined by the expression: A1>A2>A3, such that
A1 is a surface free energy of the carbon compound layer;
A2 is a surface free energy of the first diamond-like carbon layer; and
A3 is a surface free energy of the second diamond-like carbon layer, and
an occurrence of cracking and separation of the (i) carbon compound layer, the (ii) first diamond-like carbon layer, and the (iii) second diamond-like carbon layer is effectively prevented in the medical instrument.

* * * * *